United States Patent
Klimowicz et al.

(10) Patent No.: US 6,543,443 B1
(45) Date of Patent: Apr. 8, 2003

(54) METHODS AND DEVICES FOR NEBULIZING FLUIDS

(75) Inventors: Michael Klimowicz, Los Altos, CA (US); Richard Stevens, San Jose, CA (US); Paul Uster, Tracy, CA (US); Joseph Maxwell, Mountain View, CA (US); Markus Flierl, Sunnyvale, CA (US)

(73) Assignee: Aerogen, Inc., Sunnyvale, CA (US)

( * ) Notice: Subject to any disclaimer, the term of this patent is extended or adjusted under 35 U.S.C. 154(b) by 0 days.

(21) Appl. No.: 09/614,306

(22) Filed: Jul. 12, 2000

(51) Int. Cl.$^7$ .............................................. A61M 11/00
(52) U.S. Cl. ..................... 128/200.23; 128/200.14; 128/200.16; 128/203.12; 239/338
(58) Field of Search ................. 128/200.14, 200.16, 128/200.19, 200.23, 200.22, 203.12, 203.22, 203.21; 604/87, 200, 244; 239/338

(56) References Cited

U.S. PATENT DOCUMENTS

| | | | |
|---|---|---|---|
| 2,101,304 A | 12/1937 | Wright | 120/50 |
| 2,158,615 A | 5/1939 | Wright | 120/50 |
| 2,187,528 A | 1/1940 | Wing | 120/50 |
| 2,223,541 A | 12/1940 | Baker | 120/50 |
| 2,266,706 A | 12/1941 | Fox et al. | 128/173 |
| 2,283,333 A | 5/1942 | Martin | 120/50 |
| 2,292,381 A | 8/1942 | Klagges | 120/50 |
| 2,360,297 A | 10/1944 | Wing | 120/52 |
| 2,375,770 A | 5/1945 | Dahlberg | 120/52 |
| 2,404,063 A | 7/1946 | Healy | 120/51 |
| 2,430,023 A | 11/1947 | Longmaid | 120/52 |
| 2,474,996 A | 7/1949 | Wallis | 120/52 |
| 2,512,004 A | 6/1950 | Wing | 120/52 |
| 2,521,657 A | 9/1950 | Severy | 120/50 |
| 2,681,041 A | 6/1954 | Zodtner et al. | 120/50 |
| 2,779,623 A | 3/1957 | Eisenkraft | 299/1 |
| 2,935,970 A | 5/1960 | Morse et al. | 120/52 |
| 3,411,854 A | 11/1968 | Rosler et al. | 401/227 |
| 3,558,052 A | 1/1971 | Dunn | 293/3 |
| 3,738,574 A | 6/1973 | Guntersdorfer et al. | 239/102 |
| 3,790,079 A | 2/1974 | Berglund et al. | 239/3 |
| 3,804,329 A | 4/1974 | Martner | 239/4 |
| 3,812,854 A | 5/1974 | Michaels et al. | 128/194 |

(List continued on next page.)

FOREIGN PATENT DOCUMENTS

| | | |
|---|---|---|
| CH | 477 885 | 10/1969 |
| CH | 555 681 | 9/1974 |
| EP | 0 049 636 A1 | 4/1982 |
| EP | 0 103 161 A2 | 3/1984 |
| EP | 0 134 847 A1 | 3/1985 |
| EP | 0 178 925 | 4/1986 |
| EP | 0 542 723 A2 | 5/1993 |

OTHER PUBLICATIONS

Berglund, R.N., et al. Generation of Monodisperse Aerosol Standards. Environ. Sci. Technology 7:2:147 (1973).

Allen, T. Particle Size Measurement. Chapman and Hall pp. 167–169 (1981).

Ueha, S., et al. Mechanism of Ultrasonic Atomization Using a Multi–Pinhole Plate. J. Acoust. Soc. Jpn. (E) 6,1:21 (1985).

Maehara, N., et al. Influence of the Vibrating System of a Multipinhole–plate Ultrasoic Nebulizer on Its Performance. Review of Scientific Instruments, 57 (11), Nov. 1986, pp. 2870–2876.

(List continued on next page.)

*Primary Examiner*—Aaron J. Lewis
*Assistant Examiner*—Darwin P. Erezo
(74) *Attorney, Agent, or Firm*—Townsend and Townsend and Crew LLP (57) ABSTRACT

A nebulizing device having two or more nebulizing elements. The nebulizing device may be used to deliver two or more fluids to the patient or may be used for enhanced fluid flow of a single fluid. The nebulizing elements are preferably vibrating elements with holes therein through which the fluid is expelled when the vibrating elements are vibrated.

22 Claims, 8 Drawing Sheets

U.S. PATENT DOCUMENTS

| | | |
|---|---|---|
| 3,950,760 A | 4/1976 | Ilse-dore Stromberger et al. ........ 346/140 |
| 3,958,249 A | 5/1976 | DeMaine et al. ............... 346/1 |
| 3,983,740 A | 10/1976 | Danel ............................ 73/12 |
| 4,005,435 A | 1/1977 | Lundquist et al. ............. 346/1 |
| 4,083,368 A * | 4/1978 | Freezer ....................... 128/198 |
| 4,119,096 A | 10/1978 | Drews ......................... 128/194 |
| 4,159,803 A | 7/1979 | Cameto et al. ............. 239/102 |
| 4,226,236 A | 10/1980 | Genese |
| 4,240,081 A | 12/1980 | Devitt .......................... 346/75 |
| 4,261,512 A | 4/1981 | Zierenberg ................. 239/102 |
| 4,268,460 A | 5/1981 | Boiarski ........................ 261/1 |
| 4,294,407 A * | 10/1981 | Reichl et al. ............... 239/102 |
| 4,300,546 A | 11/1981 | Kruber ........................ 128/200 |
| 4,301,093 A | 11/1981 | Eck ............................... 261/1 |
| 4,334,531 A | 6/1982 | Reichl et al. .......... 128/200.14 |
| 4,336,544 A | 6/1982 | Donald et al. ............... 346/1.1 |
| 4,338,576 A | 7/1982 | Takahashi et al. ............ 331/67 |
| 4,368,476 A | 1/1983 | Uehara et al. .......... 346/140 R |
| 4,389,071 A | 6/1983 | Johnson, Jr. et al. ......... 299/14 |
| 4,408,719 A | 10/1983 | Last .......................... 239/102 |
| 4,431,136 A | 2/1984 | Janner et al. ............... 239/102 |
| 4,454,877 A | 6/1984 | Miller et al. ........... 128/200.21 |
| 4,465,234 A | 8/1984 | Maehara et al. ............ 239/102 |
| 4,474,251 A | 10/1984 | Johnson, Jr. .................. 175/67 |
| 4,474,326 A | 10/1984 | Takahashi ................... 239/102 |
| 4,475,113 A | 10/1984 | Lee et al. ...................... 346/1.1 |
| 4,479,609 A | 10/1984 | Maeda et al. ................ 239/102 |
| 4,530,464 A | 7/1985 | Yamamoto et al. ......... 239/102 |
| 4,533,082 A | 8/1985 | Maehara et al. ............ 239/102 |
| 4,539,575 A | 9/1985 | Nilsson .................. 346/140 R |
| 4,544,933 A | 10/1985 | Heinzl ..................... 346/140 R |
| 4,546,361 A | 10/1985 | Brescia et al. .......... 346/140 R |
| 4,550,325 A | 10/1985 | Viola ..................... 346/140 R |
| 4,591,883 A | 5/1986 | Isayama ................. 346/140 R |
| 4,593,291 A | 6/1986 | Howkins ..................... 346/1.1 |
| 4,605,167 A | 8/1986 | Maehara ..................... 239/102 |
| 4,620,201 A | 10/1986 | Heinzl et al. ........... 346/140 R |
| 4,628,890 A | 12/1986 | Freeman ...................... 123/593 |
| 4,632,311 A | 12/1986 | Nakane et al. ............... 239/101 |
| 4,659,014 A | 4/1987 | Soth et al. ................ 239/102.2 |
| 4,681,264 A | 7/1987 | Johnson, Jr. ............. 239/589.1 |
| 4,702,418 A | 10/1987 | Carter et al. ................. 239/101 |
| 4,722,906 A | 2/1988 | Guire |
| 4,753,479 A | 6/1988 | Murphy ....................... 417/322 |
| 4,790,479 A | 12/1988 | Matsumoto et al. ..... 239/102.2 |
| 4,793,339 A | 12/1988 | Matsumoto et al. ... 128/200.16 |
| 4,796,807 A | 1/1989 | Bendig et al. ........... 239/102.2 |
| 4,799,622 A | 1/1989 | Ishikawa et al. ......... 239/102.2 |
| 4,826,759 A | 5/1989 | Guire |
| 4,828,886 A | 5/1989 | Hieber ....................... 427/422 |
| 4,850,534 A | 7/1989 | Takahashi et al. ........ 239/102.2 |
| 4,865,006 A | 9/1989 | Nogi et al. .................. 123/590 |
| 4,877,989 A | 10/1989 | Drews et al. ................ 310/323 |
| 4,888,516 A | 12/1989 | Daeges et al. ............... 310/323 |
| 4,968,299 A | 11/1990 | Ahlstrand et al. |
| 4,973,493 A | 11/1990 | Guire |
| 4,976,259 A | 12/1990 | Higson et al. |
| 4,979,959 A | 12/1990 | Guire |
| 4,994,043 A | 2/1991 | Ysebaert |
| 5,002,048 A * | 3/1991 | Makiej, Jr. ............. 128/200.23 |
| 5,002,582 A | 3/1991 | Guire et al. |
| 5,007,419 A * | 4/1991 | Weinstein et al. ..... 128/200.23 |
| 5,021,701 A | 6/1991 | Takahashi et al. .......... 310/345 |
| 5,063,396 A | 11/1991 | Shiokawa et al. ...... 346/140 R |
| 5,063,922 A | 11/1991 | Hakkinen .............. 128/200.16 |
| 5,073,484 A | 12/1991 | Swanson et al. |
| 5,076,266 A | 12/1991 | Babaev ................. 128/200.36 |
| 5,080,649 A | 1/1992 | Vetter |
| 5,086,785 A | 2/1992 | Gentile et al. |
| 5,115,803 A | 5/1992 | Sioutas .................. 128/200.23 |
| 5,134,993 A * | 8/1992 | Van Der Linden et al. ......... 123/200.14 |
| 5,139,016 A | 8/1992 | Waser .................... 128/200.16 |
| 5,140,740 A | 8/1992 | Weigelt |
| 5,152,456 A | 10/1992 | Ross et al. ................ 239/102.2 |
| 5,157,372 A | 10/1992 | Langford |
| 5,164,740 A | 11/1992 | Ivri ............................. 346/1.1 |
| 5,169,029 A * | 12/1992 | Behar et al. ..................... 222/1 |
| 5,170,782 A | 12/1992 | Kocinski ............... 128/200.16 |
| 5,186,164 A | 2/1993 | Raghuprasad |
| 5,186,166 A | 2/1993 | Riggs et al. |
| 5,198,157 A | 3/1993 | Bechet ........................... 264/9 |
| 5,217,492 A | 6/1993 | Guire et al. |
| 5,258,041 A | 11/1993 | Guire et al. |
| 5,261,601 A * | 11/1993 | Ross et al. ................ 239/102.2 |
| 5,263,992 A | 11/1993 | Guire |
| 5,297,734 A | 3/1994 | Toda ....................... 239/102.2 |
| 5,299,739 A | 4/1994 | Takahashi et al. ....... 239/102.2 |
| 5,309,135 A | 5/1994 | Langford |
| 5,312,281 A | 5/1994 | Takashashi et al. ........... 446/25 |
| 5,320,603 A | 6/1994 | Vetter et al. |
| 5,347,998 A | 9/1994 | Hodson et al. ......... 128/200.23 |
| 5,414,075 A | 5/1995 | Swan et al. |
| 5,415,161 A | 5/1995 | Ryder .................... 128/200.23 |
| 5,419,315 A * | 5/1995 | Rubsamen ............. 128/200.14 |
| 5,437,267 A * | 8/1995 | Weinstein et al. ..... 128/200.23 |
| 5,452,711 A | 9/1995 | Gault |
| 5,477,992 A | 12/1995 | Jinks et al. ............. 222/402.16 |
| 5,487,378 A | 1/1996 | Robertson et al. ..... 128/200.16 |
| 5,512,329 A | 4/1996 | Guire |
| 5,512,474 A | 4/1996 | Clapper et al. |
| 5,515,841 A | 5/1996 | Robertson et al. ..... 128/200.16 |
| 5,515,842 A | 5/1996 | Ramseyer et al. |
| 5,518,179 A | 5/1996 | Humberstone et al. .. 239/102.2 |
| 5,529,055 A * | 6/1996 | Gueret .................. 128/200.16 |
| 5,533,497 A | 7/1996 | Ryder .................... 128/200.21 |
| 5,563,056 A | 10/1996 | Swan et al. |
| 5,579,757 A | 12/1996 | McMahon et al. ..... 128/200.21 |
| 5,586,550 A | 12/1996 | Ivri et al. ............... 128/200.16 |
| 5,609,798 A * | 3/1997 | Liu et al. ..................... 261/78.2 |
| 5,637,460 A | 6/1997 | Swan et al. |
| 5,654,162 A | 8/1997 | Guire et al. |
| 5,654,460 A | 8/1997 | Rong |
| 5,664,557 A * | 9/1997 | Makiej, Jr. ............. 128/200.23 |
| 5,665,068 A | 9/1997 | Takamura |
| 5,692,644 A | 12/1997 | Gueret |
| 5,707,818 A | 1/1998 | Chudzik et al. |
| 5,714,360 A | 2/1998 | Swan et al. |
| 5,714,551 A | 2/1998 | Bezwada et al. |
| 5,718,222 A | 2/1998 | Lloyd et al. |
| 5,744,515 A | 4/1998 | Clapper |
| 5,755,218 A * | 5/1998 | Johansson et al. ..... 128/200.14 |
| 5,758,637 A * | 6/1998 | Ivri et al. ............... 128/200.16 |
| 5,893,515 A | 4/1999 | Hahn et al. |
| 5,938,117 A | 8/1999 | Ivri .............................. 239/4 |
| 5,970,974 A * | 10/1999 | Van Der Linden et al. ......... 128/200.16 |
| 6,012,450 A | 1/2000 | Rabsamen |
| 6,014,970 A | 1/2000 | Ivri et al. |
| 6,085,740 A | 7/2000 | Ivri et al. |
| 6,186,141 B1 * | 2/2001 | Pike et al. .............. 128/203.12 |
| 6,196,219 B1 * | 3/2001 | Hess et al. ............. 128/200.21 |

FOREIGN PATENT DOCUMENTS

| | | |
|---|---|---|
| EP | 0 476 991 B1 | 3/1995 |
| FR | 2 692 569 A1 | 6/1992 |
| GB | 973458 | 10/1964 |
| GB | 1454597 | 11/1976 |

| | | |
|---|---|---|
| GB | 2 073 616 A | 10/1981 |
| GB | 2 101 500 | 1/1983 |
| GB | 2 177 623 A | 1/1987 |
| GB | 2 240 494 A | 8/1991 |
| GB | 2 272 389 A | 5/1994 |
| GB | 2 279 571 A | 1/1995 |
| JP | 57-23852 | 2/1982 |
| JP | 57-105608 | 7/1982 |
| JP | 58-61857 | 4/1983 |
| JP | 58-139757 | 8/1983 |
| JP | 60-4714 A | 1/1985 |
| JP | 61-8357 A | 1/1986 |
| JP | 61-215059 A | 9/1986 |
| JP | 2-135169 | 5/1990 |
| JP | 2-189161 | 7/1990 |
| WO | WO 92/07600 | 5/1992 |
| WO | WO 92/11050 | 7/1992 |
| WO | WO 93/01404 | 1/1993 |
| WO | WO 96/09229 | 3/1996 |
| WO | WO 96/31289 | 10/1996 |
| WO | WO 97/07896 | 3/1997 |
| WO | WO 99/63946 | 12/1999 |

OTHER PUBLICATIONS

Maehara, N., et al. Optimum Design Procedure for Multi–Pinhole–plate Ultrasonic Atomizer. Japanese Journal of Applied Physics, 26:215 (1987).

Ashgriz, N., et al. Development of a Controlled Spray Generator. Rev. Sci. Instrum. 58(7):1291 (1987).

Hikayama, H., et al. Ultrasonic Atomizer with Pump Function. Tech. Rpt. IEICE Japan US88–74:25 (1988).

J. Acoustical Soc. Japan 44:2:116 (1988).

J. Acoustical Soc. Japan 44:6:425 (1988).

Siemens AG, 1989, "Ink–Jet Printing: The Present State of The Art," by Wolfgang R. Wehl.

TSI Incorporated product catalog. Vibrating Orifice Aerosol Generator (1989).

Gaiser Tool Company catalog, pp. 26, 29–30 (19__).

Nogi, T., et al. Mixture Formation of Fuel Injection System in Gasoline Engine. Nippon Kikai Gakkai Zenkoku Taikai koenkai Koen Ronbunshu 69:660 (1991).

D.C. Cipolla et al., "Assesment of Aerosol Delivery Systems for Recombinant Human Deoxyribonuclease," STP Pharma Sciences 4 (1) 50–62, 1994.

D.C. Cipolla et al., "Characterization of Aerosols of Human Recombinant Deoxyribonuclease I (rhDNase) Generated by Jet Nebulizers," Pharmaceutical Research II 94) 491–498, 1994.

I. Gonda,. "Therapeutic Aerosols," Pharmaceutics, The Sci. of Dosage Form Design, M.E. Aulton, 341–358, 1988.

Anthony J. Hickey, "Pharmaceutical Inhalation Aerosol Technology," Drugs and the Pharmaceutical Sciences, (54) 172–173.

* cited by examiner

METHODS AND DEVICES FOR NEBULIZING FLUIDS

BACKGROUND OF THE INVENTION

The present invention is directed to methods and devices for nebulizing fluids. In a specific application of the present invention, the device is used to nebulize fluids for delivery to the lungs. Although the present invention is particularly useful for nebulizing fluids for inhalation, it is understood that the present invention may be used for nebulizing fluids in other fields and for other purposes.

SUMMARY OF THE INVENTION

In a first aspect of the present invention, a nebulizing device is provided which has at least two nebulizing elements. In a preferred embodiment, the nebulizing element has a vibrating element with a plurality of apertures. The vibrating element is preferably a relatively stiff element, such as a rigid dome-shaped element, but may be any other suitable structure. The vibrating elements are vibrated to expel fluid through the apertures.

The device may be operated to provide independent delivery of two different fluids. In a specific application of the present invention for nebulizing liquids for inhalation, the first fluid may contain an immune modulator or a mucolytic, such as alpha dornase, and the second fluid could contain an antibiotic, such as an aminoglycocide like tobramicin, or quinolone, pentamidine, or an antifungal such as amphotericin B. Another application for the device is for the first fluid to contain a short acting beta agonist and the second fluid to contain a corticosteroid. The beta agonist provides symptomatic relief and the corticosteroid treats the underlying immune reaction. The beta agonist may be any suitable beta agonist such as albuterol. These drugs complement one another in the treatment of asthma. Other combinations of drugs may be delivered with the device which relate to the same ailment or to different ailments.

The first and second fluids may also be delivered in the same breath. In one aspect, the first fluid may be delivered earlier than the second fluid. For example, the first fluid could contain a bronchodilator which opens the lungs for delivery of the second fluid. Alternatively, the second fluid could be a bronchorestrictor delivered after the first fluid to help retain the first fluid in the lungs. Of course, any combinations of liquids may be delivered as the first and second fluids and the examples given are merely illustrative.

Although the device may be operated to deliver two or more fluids, the device may be used to deliver a single fluid. When delivering only one fluid, the combination of nebulizers provides enhanced flow. For example, the nebulizing elements may together be used to deliver 40–300 microliters, more preferably 100–250 microliters, in one breath. Stated another way, the nebulizing elements are used to deliver at least 100 microliters and more preferably at least 200 microliters of fluid in one breath by the user. Stated still another way, the device delivers the preferred amounts in no more than four seconds of operating time. The first and second nebulizers also provide the ability to provide relatively large increases and decreases in fluid flow rate by simply activating or de-activating one or more of the nebulizers. Of course, the flow rate of each of the nebulizers may be adjusted by changing the power or frequency of operation.

In another aspect of the present invention, the nebulizer may also instruct or permit the user to inhale a set number of doses over a period of time. For example, the device may permit and/or instruct the user to inhale six doses of the first fluid, such as a beta agonist, per day and only two doses of the second fluid, such as a corticosteroid. The control system may also permit a set number of doses of one of the fluids in relation to the amount of the other fluid delivered. In this manner, the relative amounts of the two fluids can be regulated.

These and other advantages and features will become apparent with the following description of the preferred embodiments, drawings and claims.

DESCRIPTION OF THE SPECIFIC EMBODIMENTS

Figure 1:
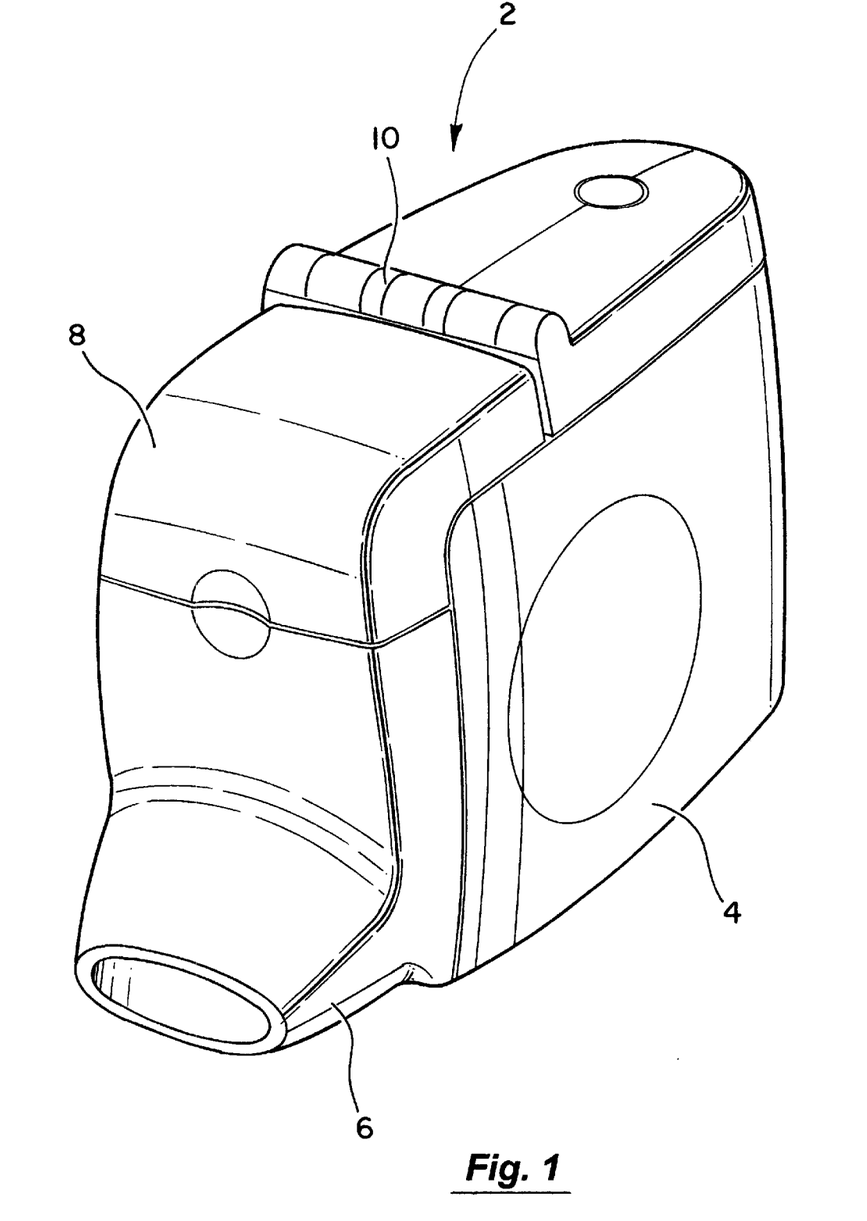
FIG. 1 is an isometric view of a device in accordance with the present invention.
Figure 2:
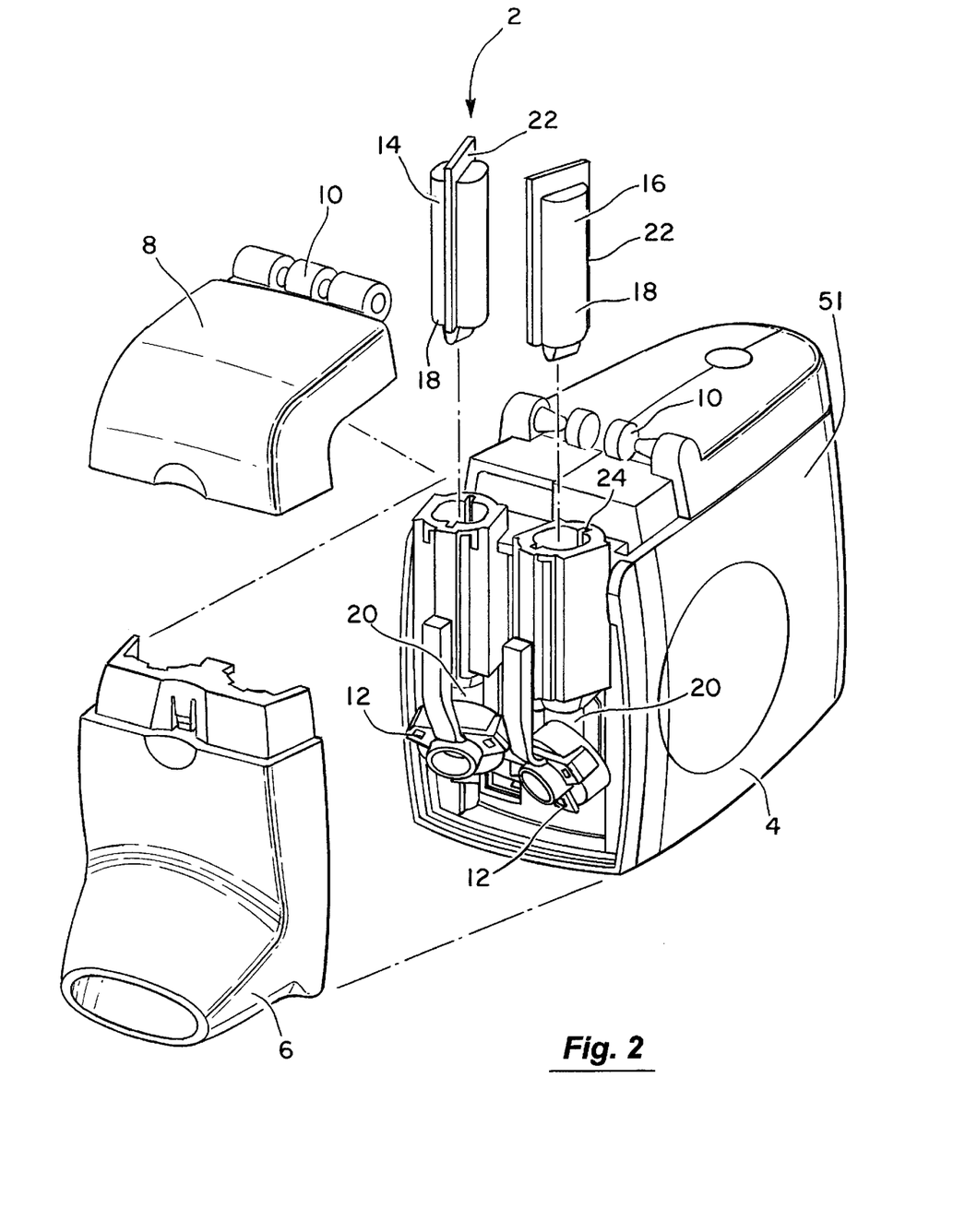
FIG. 2 shows the device with a door and mouthpiece removed to expose internal components of the device.
Figure 3:
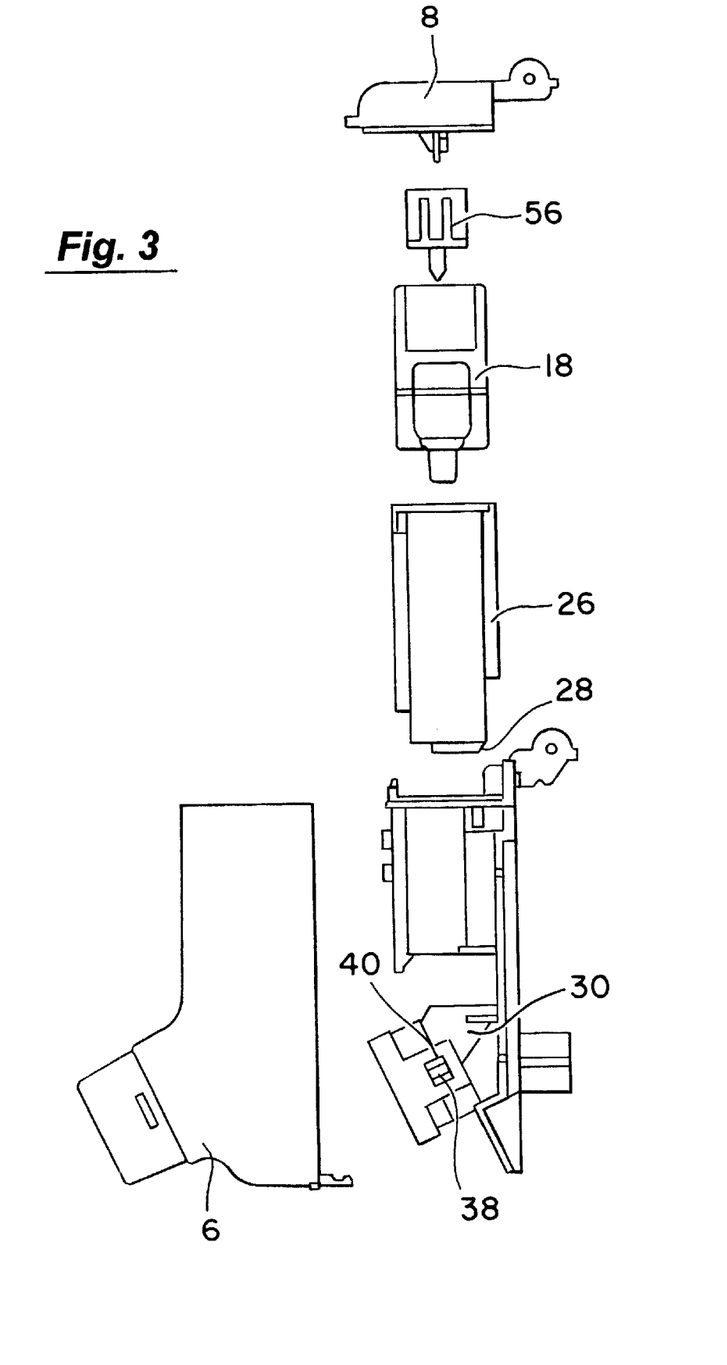
FIG. 3 is a side view of another fluid delivery system for the device.
Figure 4:
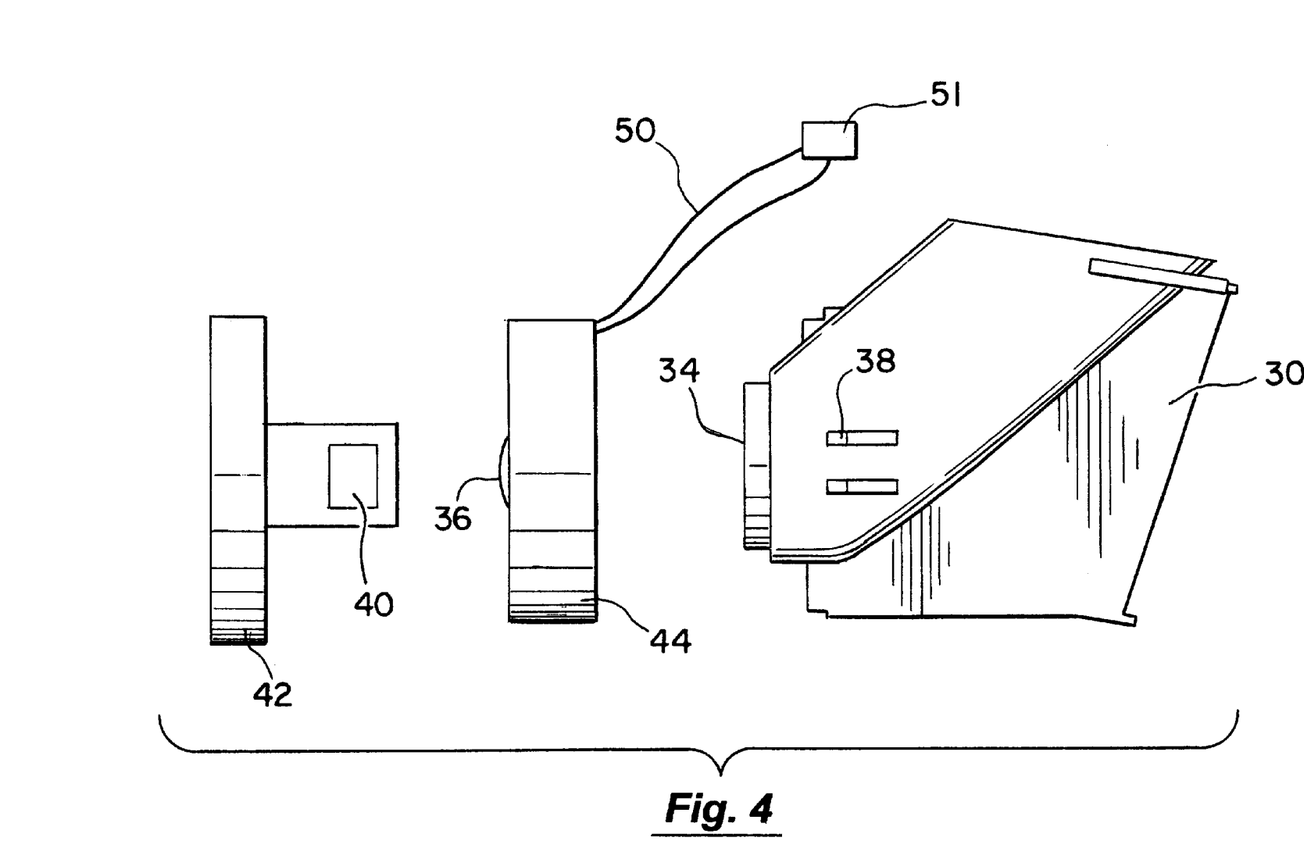
FIG. 4 is an exploded side of a vibrating element and a fluid receptacle.
Figure 5:
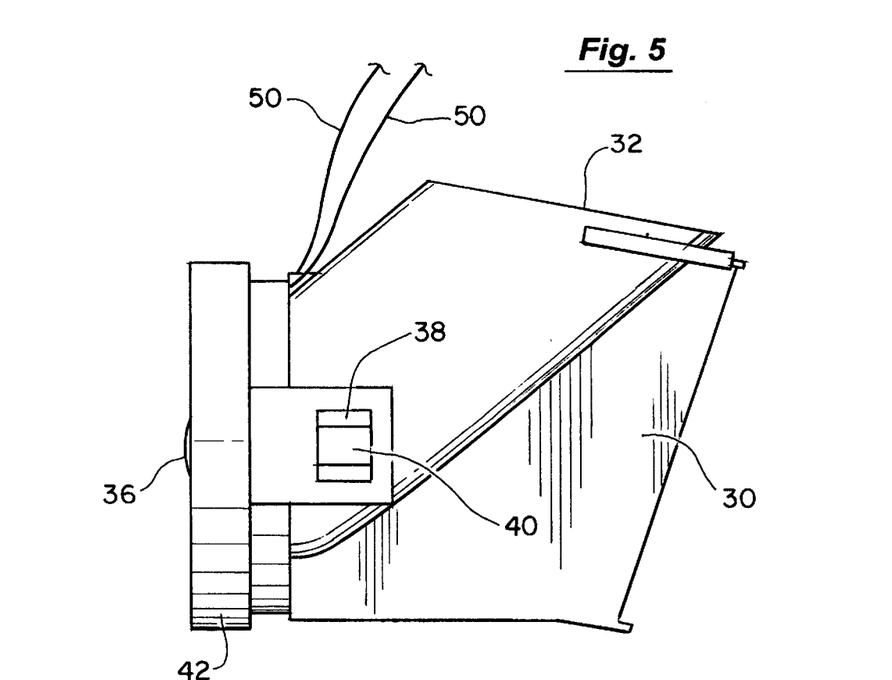
FIG. 5 is a side view of the vibrating element and fluid receptacle.
Figure 6:
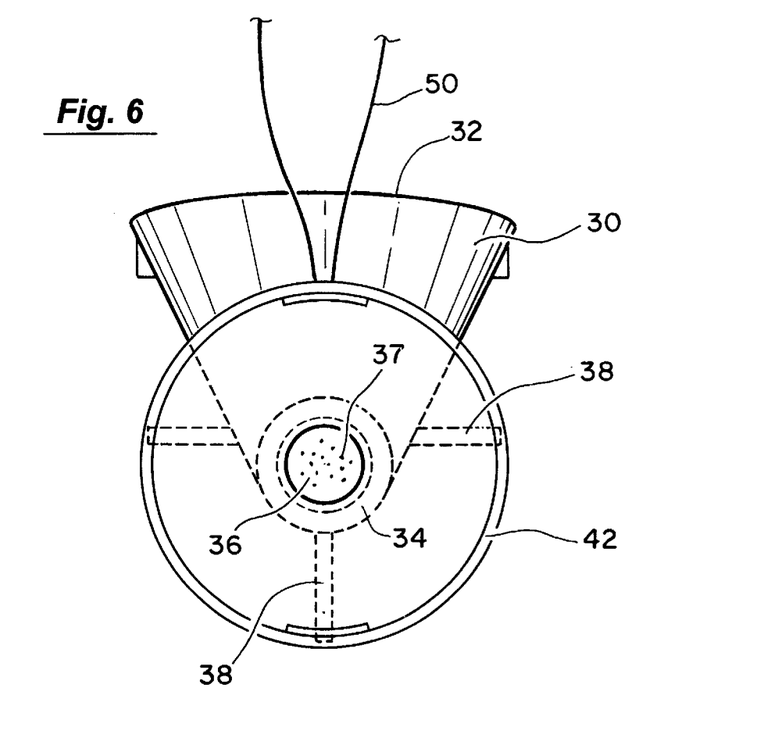
FIG. 6 is an end view of the assembly of FIG. 5.
Figure 7:
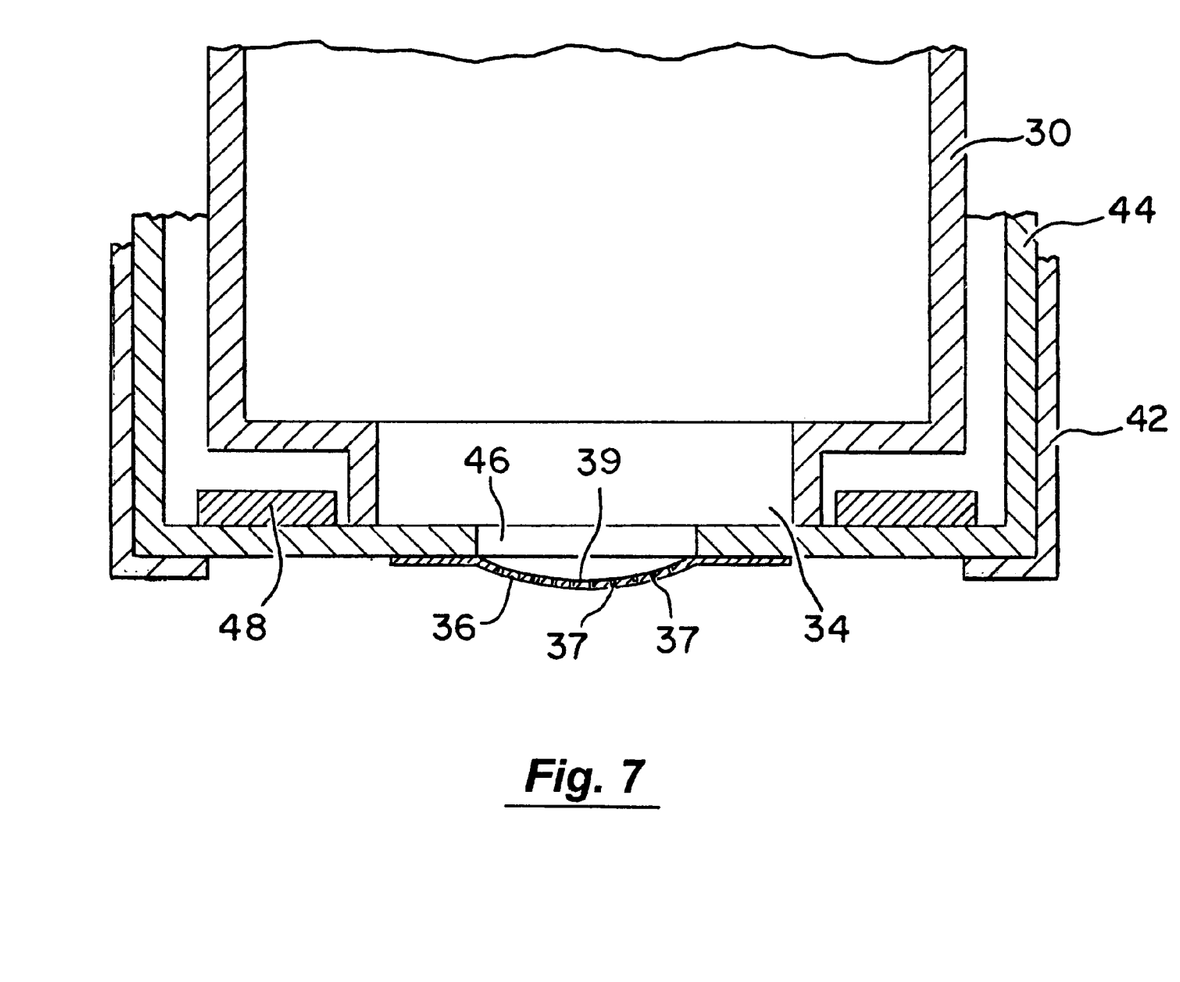
FIG. 7 is a cross-sectional view of an end of the assembly of FIG. 5 around line A—A.
Figure 8:
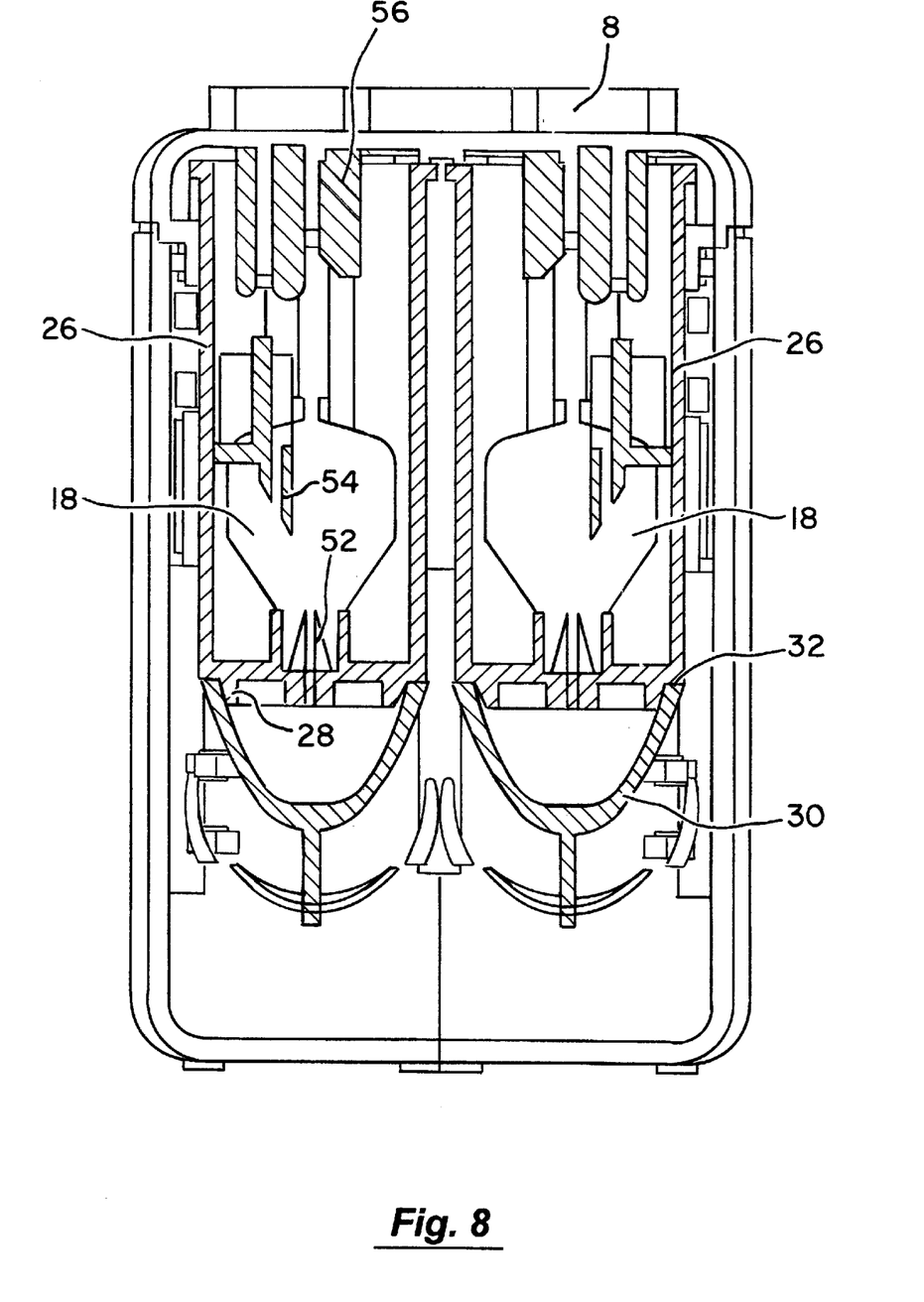
FIG. 8 is a partial cross-sectional view of the fluid delivery system for the device of FIGS. 3–7.

Referring to FIGS. 1 and 2, a nebulizing device 2 is shown. The nebulizing device 2 includes a housing 4 having a mouthpiece 6 and a door 8. The door 8 and mouthpiece 6 are removed in FIG. 2. The door 8 is coupled to the housing 4 with hinges 10 to open and close the door 8. As explained above, the nebulizing device 2 of the present invention may be used for a number of different applications and a preferred application is as a hand-held, portable device for delivery of at least one fluid to the lungs.

In one aspect of the invention, the nebulizing device 2 has at least two nebulizing elements 12. As will be described in greater detail below, the nebulizing elements 12 provide the ability to control the delivery of two different drugs to the patient. This can be important when two or more drugs are delivered to treat the same ailment. The drugs may be delivered at the same time or at different times in a controlled manner. The combination of nebulizing elements 12 also provides high flow rates when only a single drug is delivered with the nebulizing elements 12.

The fluid is contained in first and second fluid cartridges 14, 16. The fluid may be contained in any suitable container and a preferred container is an ampoule 18. The fluid may be delivered from the cartridges 14, 16 to the nebulizing elements 12 in any manner. A capillary feed system 20 and a system for delivering single doses are described below. The device 2 is designed so that the fluid cartridges 14, 16 can be replaced a number of times for subsequent use. It is understood that the fluid may be delivered in any other manner such as delivering a number of discrete volumes from a capsule using a piston.

The device 2 may be similar in construction and design to the devices described in U.S. Pat. No. 5,758,637 and U.S.

Pat. No. 6,014,970, which are hereby incorporated by reference, although any other suitable structure may be used. The ampoule 18 preferably has a flange 22 which registers with slots 24 in the device 2. Fluid from the cartridge 14 is delivered to the nebulizing elements 12 with the capillary feed system 20 such as the capillary feed systems described in U.S. Pat. No. 5,938,117 and U.S. Pat. No. 5,758,637 which are incorporated here by reference.

Referring to FIGS. 3–8, another fluid delivery system is shown which is an alternative to the capillary system 20 described in connection with FIGS. 1 and 2. The system is designed to receive single dose ampoules 18 which are replaced after each use. The ampoule 18 fits within an adapter 26. The adapter 26 and ampoule 18 are preferably packaged together as a unit but may also be separate. The adapter 26 has a lip 28 which engages a fluid receptacle 30. The fluid receptacle 30 is large enough to accommodate the entire volume of the ampoule 18. In the preferred embodiment, the fluid receptacle 30 holds about 15 microliters to 2 milliliters and preferably about 500 microliters.

The fluid receptacle 30 is generally funnel-shaped and extends upward to an opening 32 which mates with the adapter 26. The fluid receptacle 30 has a second opening 34 which fits around a vibrating element 36. The vibrating element 36 has openings 37 therein and a backside 39 exposed to fluid in the fluid receptacle 30. Lateral tabs 38 extend from the receptacle 30 and engage an opening 40 in a holder 42. The vibrating element 36 is mounted around an opening 46 in a cup-shaped element 44 and the cup-shaped element is held within the holder 42. The vibrating element 36 has the apertures 37 through which fluid is expelled when the element 36 is vibrated. The receptacle 30 is preferably adhered to the element 36 with an adhesive such as silicone. The vibrating element 36 is vibrated with a ring-shaped piezoelectric member 48 mounted to the holder 42. Wires 50 connect the piezoelectric member 48 to a control system 51. The nebulizing element 12 may be any suitable device or structure and is preferably dome-shaped and manufactured in the manner described in U.S. Pat. No. 6,014,970 incorporated above.

The ampoule 18 is pierced by a first spike 52 which delivers fluid from the cartridge 14, 16 to the receptacle 30. The first spike 52 is mounted to the adapter 26 and is replaced with the adapter after each use. A second spike 54 introduces air into the cartridge 14, 16 as fluid is drained into the receptacle 30 for smooth delivery of the fluid. The first and second spikes 52, 54 automatically pierce the cartridge 14, 16 when the door 8 is closed. The second spike 54 is mounted to a top 56 which is driven into the receptacle 30 when the door 8 is closed. Although the fluid is delivered to the nebulizing element 12 in finite amounts or with capillary feed, the fluid may also be delivered to the nebulizing elements 12 in any other manner. For example, the fluid cartridge 14, 16 may contain a number of doses with the dose size being selected using conventional methods of delivering small amounts of fluid.

Figure 9:
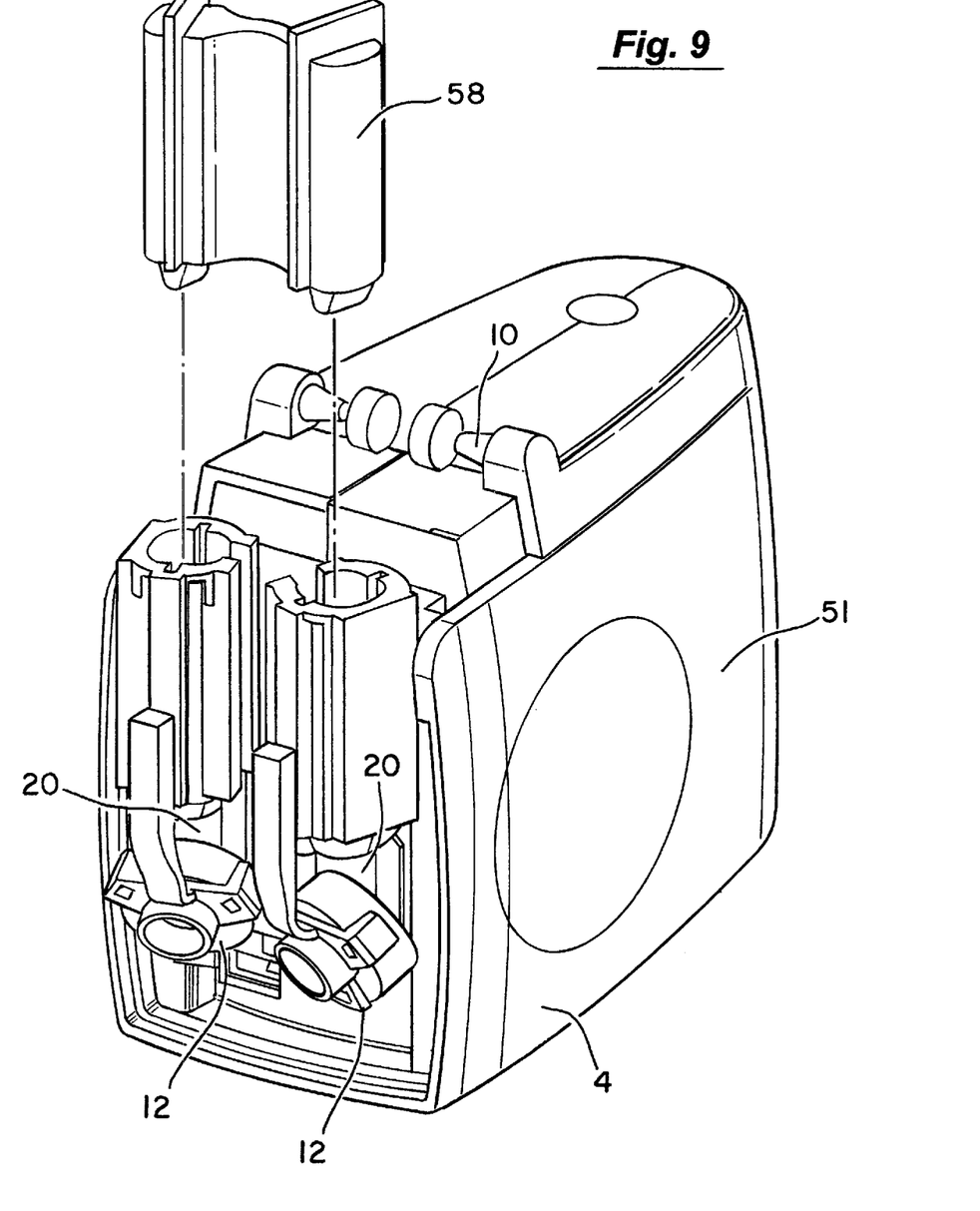
FIG. 9 shows a single fluid container.

Referring to FIG. 9, the device 2 may also have a single fluid cartridge 58. The fluid cartridge 58 may contain separate compartments for two different fluids. The fluid cartridge 58 may also simply contain a single fluid which is delivered to both nebulizing elements 12. When delivering only one fluid, the combination of nebulizers 12 provides the ability to produce large flow rates. For example, the nebulizing elements 12 may together be used to deliver 40–300 microliters, more preferably 100–250 microliters, in one breath. Stated another way, the nebulizing elements 12 are used to deliver at least 100 microliters and more preferably at least 200 microliters of fluid in one breath by the user. The nebulizing elements 12 also occupy a relatively small area so that the device is compact. The first and second nebulizers 12 also provide the ability to provide relatively large increases and decreases in fluid flow rate by simply activating or de-activating one or more of the nebulizers 12. Of course, the flow rate through each of the nebulizers may be adjusted by changing the power and/or frequency of operation.

The control system 51 controls the nebulizing elements and/or instructs the user on use of the device 2. The device has one or more indicators which may be audible or visual such as a clock, timer, or display which tells the user when and/or how to use the device. In a preferred embodiment, the indicator indicates one of more of the following: when the user should take a dose of one or more of the fluids, when the fluid is ready for inhalation, when the nebulizing element has been activated, and/or upon completion of a breath hold time. In one mode of operation, the indicator is simply a light. The user loads one or more cartridges 14, 16 and closes the door to deliver the fluid to the receptacle 30. When the dose is ready, the green light may flash which indicates that the user may activate the device 2. The device may be actuated with a button (not shown) or with a flow activated sensor. The light may remain on when the nebulizing element 12 has been activated and remains illuminated until a breath hold period is completed. The breath hold period may be set to be any value such as five seconds after completing delivery of the fluid. The visual indicators described herein are merely an example of a system for controlling and instructing the user in use of the device and many other variations for the control system may be used without departing from various aspects of the invention.

The device 2 may be operated in various other modes now described. Of course, the device 2 may operate in still different modes without departing from various aspects of the invention. In a first mode of operation, the first and second fluids may be delivered in the same breath or may be delivered independently. In a specific application of the present invention, the first fluid may contain a mucolytic, such as alpha dornase, and the second fluid may contain an antibiotic, such as an aminoglycocide like tobramicin, or quinolone, pentamidine, or an antifungal such as amphotericin B. The control system 51 may also permit and prevent a set number of doses over a period of time. For example, the nebulizing device 2 may permit the user to have a set number of doses of the first fluid, such as six doses of the beta agonist per day, while permitting another set number of doses of the second fluid, such as two doses of the corticosteroid per day. In this manner, a single device 2 may be used to control the relative delivery of two different fluids.

The control system 51 may also operate to deliver the first and second fluids in the same breath. For example, the first fluid may be delivered before completing delivery of the second fluid. When operating in this mode, the first fluid may contain any suitable fluid such as a bronchodilator which opens the lungs in preparation for receiving the second fluid. The second fluid may be also delivered after the first or "main" fluid. The second fluid may be any suitable fluid such as a bronchorestrictor. Of course, the first and second fluids may be delivered simultaneously for a period of time without departing from the scope of the invention.

Finally, the control system 51 may operate to deliver different amounts of the first and second fluids in any of the modes described above. For example, the first fluid may be a short acting insulin and the second fluid may be a long acting insulin. The control system 51 may deliver different amounts of the two fluids such as twice as much short acting insulin as long acting insulin.

The invention has been described by way of the preferred embodiments, the invention should not be limited to the specific embodiments since various modifications and changes can be incorporated without departing from the scope of the invention. For example, the nebulizing elements may be relatively flat elements, the fluid container may be a titratable capsule, and the device may have three or more nebulizers. Finally, the invention has been described with respect to various features and aspects of the invention and it is understood that these features and aspects are independent of one another and none of the features or aspects should be considered essential or indispensable relative to the other features and aspects. For example, aspects of the fluid delivery system may be practiced with a device having only one nebulizing element and aspects of the multi-nebulizer device may be practiced with an entirely different fluid delivery system.

What is claimed is:

1. A method of nebulizing a substance, comprising the steps of:
   providing a device having a housing, a first nebulizer, and a second nebulizer, the first and second nebulizers being mounted within the housing;
   delivering fluid to the first and second nebulizers, the fluid delivering step being carried out with a fluid cartridge mounted to the housing, the fluid being delivered to both the first and second nebulizers from the cartridge, the fluid delivering step being carried out with the fluid cartridge having a first fluid container containing a first fluid and a second fluid container containing a second fluid, the first fluid container supplying the first fluid to the first nebulizer and the second fluid container supplying the second fluid to the second nebulizer;
   activating the first and second nebulizers thereby nebulizing the fluid.

2. The method of claim 1, wherein:
   the providing step is carried out with the first nebulizer having a first vibrating element having a first plurality of apertures and the second nebulizer has a second vibrating element having a second plurality of apertures.

3. The method of claim 1, wherein:
   the fluid delivering step is carried out with the first fluid being a fluid selected from the group consisting of beta-agonist, mucolytic, and an immune modulator and the second fluid is a fluid selected from the group consisting of an antibiotic, an antifungal, and a corticosteroid.

4. The method of claim 1, wherein:
   the activating step is carried out with the first and second nebulizers being activated for different lengths of time.

5. The method of claim 1, wherein:
   the activating step is carried out with the first and second nebulizers being activated at the same time.

6. The method of claim 1, wherein:
   the delivering step is carried out with discrete volumes of fluid being delivered to the first and second nebulizers.

7. The method of claim 1, wherein:
   the providing step is carried out with the housing having a mouthpiece; and
   the method further comprising the step of inhaling through the mouthpiece to deliver the nebulized fluid to the lungs.

8. The method of claim 1, wherein:
   the delivering step is carried out by delivering 40–300 microliters of fluid in one breath.

9. The method of claim 8, wherein:
   the delivering step is carried out by delivering at least 100 microliters in one breath.

10. The method of claim 8, wherein:
    the delivering step is carried out by delivering at least 200 microliters of fluid in one breath.

11. The method of claim 10, wherein:
    the delivering step is carried out by delivering the amount in less than four seconds.

12. A method of nebulizing a substance, comprising the steps of:
    providing a device having a housing, a first nebulizer, and a second nebulizer, the first and second nebulizers being mounted within the housing;
    delivering fluid to the first and second nebulizers, the fluid delivering step being carried out with a fluid cartridge mounted to the housing, the fluid being delivered to both the first and second nebulizers from the cartridge;
    activating the first and second nebulizers thereby nebulizing the fluid, the activating step being carried out with the first and second nebulizers being activated at the same time.

13. The method of claim 12, wherein:
    the providing step is carried out with the first nebulizer having a first vibrating element having a first plurality of apertures and the second nebulizer has a second vibrating element having a.second plurality of apertures.

14. The method of claim 12, wherein:
    the fluid delivering step is carried out with the fluid cartridge having a first fluid container containing a first fluid and a second fluid container containing a second fluid, the first fluid container supplying the first fluid to the first nebulizer and the second fluid container supplying the second fluid to the second nebulizer.

15. The method of claim 14, wherein:
    the fluid delivering step is carried out with the first fluid being a fluid selected from the group consisting of beta-agonist, mucolytic, and an immune modulator and the second fluid is a fluid selected from the group consisting of an antibiotic, an antifungal, and a corticosteroid.

16. The method of claim 12, wherein:
    the activating step is carried out with the first and second nebulizers being activated for different lengths of time.

17. The method of claim 12, wherein:
    the delivering step is carried out with discrete volumes of fluid being delivered to the first and second nebulizers.

18. The method of claim 12, wherein:
    the providing step is carried out with the housing having a mouthpiece; and
    the method further comprising the step of inhaling through the mouthpiece to deliver the nebulized fluid to the lungs.

19. The method of claim 12, wherein:

the delivering step is carried out by delivering 40–300 microliters of fluid in one breath.

20. The method of claim 19, wherein:

the delivering step is carried out by delivering at least 100 microliters in one breath.

21. The method of claim 19, wherein:

the delivering step is carried out by delivering at least 200 microliters of fluid in one breath.

22. The method of claim 21, wherein:

the delivering step is carried out by delivering the amount in less than four seconds.

* * * * *